United States Patent [19]

Nyzen

[11] Patent Number: 5,680,436

[45] Date of Patent: *Oct. 21, 1997

[54] APPARATUS FOR MOUNTING A CYLINDRICAL ITEM, SUCH AS AN X-RAY TUBE, TO A SURFACE

[76] Inventor: Richard C. Nyzen, 620 Merriman Rd., Akron, Ohio 44303

[*] Notice: The term of this patent shall not extend beyond the expiration date of Pat. No. 5,533,090.

[21] Appl. No.: 581,832

[22] Filed: Jan. 2, 1996

Related U.S. Application Data

[63] Continuation-in-part of Ser. No. 335,165, Nov. 7, 1994, Pat. No. 5,533,098.

[51] Int. Cl.⁶ .................................................... H05G 1/02
[52] U.S. Cl. ................ 378/197; 378/193; 248/316.4
[58] Field of Search ................................ 378/167, 197, 378/168, 170, 193, 204, 205, 206; 248/62, 74.1, 316.1, 316.4, 316.5

[56] References Cited

U.S. PATENT DOCUMENTS

| | | | |
|---|---|---|---|
| 2,420,002 | 5/1947 | McKay | 248/316.1 |
| 2,727,325 | 12/1955 | Jurinic | 248/316.1 X |
| 3,228,639 | 1/1966 | Korns | 248/62 |
| 3,492,482 | 1/1970 | Forsyth | 250/93 |
| 3,668,392 | 6/1972 | Bajek et al. | 250/43.5 D |
| 3,790,803 | 2/1974 | Phillips | 250/490 |
| 4,002,915 | 1/1977 | Weiss et al. | 250/490 |
| 4,092,544 | 5/1978 | Grim | 250/491 |
| 4,246,486 | 1/1981 | Madsen | 250/491 |
| 4,255,657 | 3/1981 | Lescrenier | 250/322 |
| 5,023,899 | 6/1991 | Ohlson | 378/196 |
| 5,067,144 | 11/1991 | Aitkenhead et al. | 378/146 |
| 5,224,680 | 7/1993 | Greenstein et al. | 248/316.4 |
| 5,385,324 | 1/1995 | Pryor et al. | 248/316.4 |
| 5,533,090 | 7/1996 | Nyzen | 378/197 |

FOREIGN PATENT DOCUMENTS 740 658   5/1943   Germany .

OTHER PUBLICATIONS

"Instrumentarium Imaging", Instrumentarium Imaging, Inc., 300 W. Edgerton Ave., Milwaukee, WI 53207, 1 page, (undated).
The MDS Ultra–Ceph, Mid–American Dental Specialties, Inc., P.O. Box 1975, Hickory Hills, IL 60455, 4 pages, (undated).
"The PC–1000/Laser 1000 Pan/Ceph Combination", Panoramic Corporation 4321 Goshen Rd., Fort Wayne, IN 46818, 1 page, (undated).
"Olympic Controls New Modular X–Ray Systems", Olympic Controls Corp. fax news letter, 1 page, (Nov. 26, 1991).
"XR 100 Tube Slide", Optima Imaging, Inc. product data sheet, 2 pages, (1995).
"XR 200 Wall Stands", Optima Imaging, Inc. product data sheet, 2 pages (1995).

Primary Examiner—David P. Porta
Attorney, Agent, or Firm—Renner, Kenner, Greive, Bobak, Taylor & Weber

[57] ABSTRACT

A system (60) for mounting a cylindrical item such as an x-ray tube (18) or pipe (73) to a flat surface includes a plate (63) having a slot (67) therein. A clamp arm (69) is rotatably carried on a bolt (68) so that it is spaced from the plate (63). The cylindrical item may be received in that space and clamped between the clamp arm (69) and the slot (67) of the plate (63) upon rotation of the clamp arm (69). The system (60) is particularly suited for a wall-mountable x-ray system (50) which includes a pair of parallel, spaced tracks (11, 12) mounted on a wall and capable of receiving, through either of their open ends (35,36), traveller assemblies (13, 14). One traveller assembly (13) carries system (60) and the other traveller assembly (14) carries x-ray receiving and patient locating equipment (16). The traveller assemblies (13, 14) are movable on the tracks (11, 12), which movement is assisted by handles (42). Handles (42) are threaded into traveller assemblies (13,14) and when the desired position along tracks (11, 12) is reached, by tightening the handles (42), the tracks (11, 12) are engaged to hold the traveller assemblies (13, 14) in place. Traveller assembly (13) may be aligned with traveller assembly (14) by use of an optical transmitter (45) carried by the traveller assembly (13) and a receiving target (47) carried by the traveller assembly (14).

21 Claims, 6 Drawing Sheets

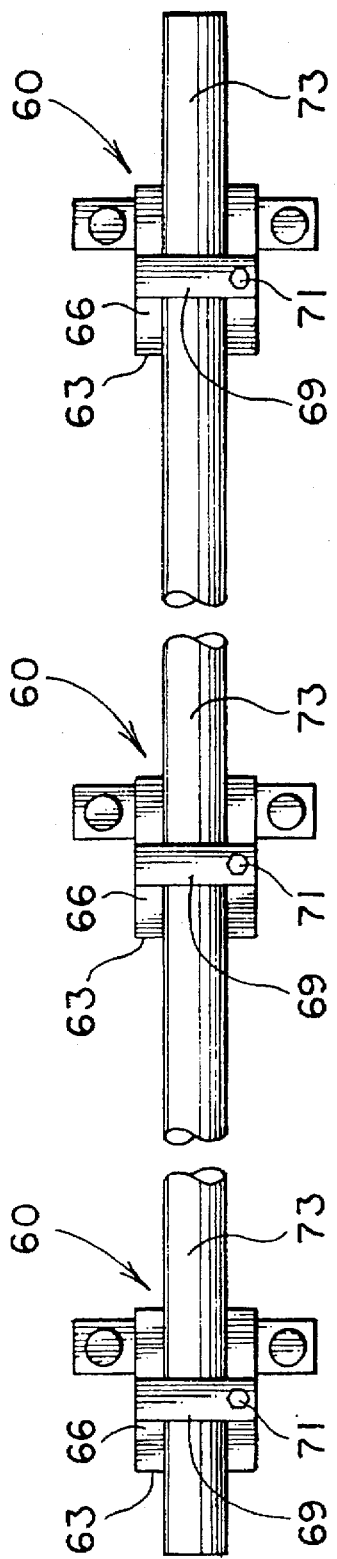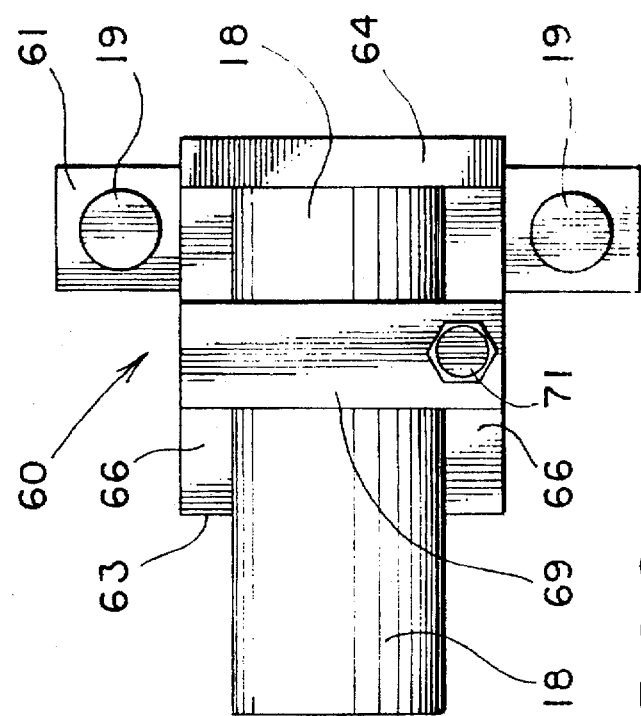
FIG. 9
FIG. 8

APPARATUS FOR MOUNTING A CYLINDRICAL ITEM, SUCH AS AN X-RAY TUBE, TO A SURFACE

CROSS-REFERENCE TO RELATED APPLICATION

This application is a continuation-in-part of patent application Ser. No. 08/335,165 which was filed on Nov. 7, 1994 now U.S. Pat. No. 5,533,098.

TECHNICAL FIELD

This invention relates to an apparatus for attaching a cylindrical item to a generally flat surface. The apparatus is particularly useful to mount an x-ray tube to x-ray equipment such as used by doctors and dentists. More particularly, this invention is specifically useful with portable x-ray equipment which can be mounted on a wall at adjustable heights and which also can align the x-ray source with the film.

BACKGROUND ART

When x-rays are to be taken, for example, in a doctor's or dentist's office, the alignment of the x-ray equipment and the adjustment thereof to correspond to the position or location of the patient's anatomy to be x-rayed is critical. For example, for cephalometric x-rays utilized by both doctors and dentists, the patient's head must be precisely aligned between the x-ray source and the film, and the source and the film must be aligned and separated by approximately five feet.

A problem occurs, of course, because patients are obviously of different heights. Thus, in one known cephalometric x-ray machine, a large arm of at least five feet in length is motorized and is vertically movably mounted on a wall. Near one end of the arm, the film holder and a head holding device extend laterally into the room. Near the other end of the arm, an x-ray tube holder likewise extends laterally outwardly into the room. The patient merely stands adjacent to the arm and the motor is activated to position the head holding device around the patient's head.

In another known cephalometric x-ray system, the equipment is mounted in a fixed position on a wall and a chair for the patient is positioned in line with the head holder. The chair is motorized to move vertically to the proper position depending on the sitting height of the patient.

There are essentially identical drawbacks to both of these prior art systems. First, both are quite expensive. The movable version requires a large arm and the controls to move the same. The fixed version requires the expensive movable chair. Moreover, both versions tie up a significant amount of space in the physician's or dentist's office. The x-ray equipment takes up more than five feet of wall space and extends out into the room a significant distance—which distance is even more compounded when the chair is required. Such is a particular waste of space when it is considered that the equipment is only used occasionally, as is the case with most dentists, for example, who must have the equipment for, but only occasionally use or need, full head or cephalometric x-rays. Thus, during the vast majority of the time, these expensive devices are merely wasting valuable office space.

In addition, for any type of x-ray device, the cylindrical x-ray tube is usually permanently associated therewith. Such is impractical as these tubes are expensive and a physician's office may have several x-ray units, all having such an x-ray tube. To date, no system has been developed to enable the x-ray user to employ a single tube for multiple pieces of equipment in that no simple manner of quickly attaching this cylindrical item to the x-ray equipment has been devised.

Thus, the need exists for inexpensive x-ray systems to which an x-ray tube may be quickly attached thereto and/or detached therefrom. Moreover, in a general sense, the need exists to be able to quickly attach any cylindrical item to a differently configured, for example, flat surface in applications other than x-ray equipment.

DISCLOSURE OF THE INVENTION

It is thus an object of the present invention to provide a system for quickly attaching a cylindrical item to another surface.

It is another object of the present invention to provide a system, as above, which has particular applicability for attaching an x-ray tube to x-ray equipment.

It is thus an object of the present invention to provide a system, as above, which can be conveniently used with x-ray equipment that is readily positionable with respect to the patient to be x-rayed.

It is another object of the present invention to provide a system, as above, usable with x-ray equipment in which the x-ray source is readily aligned with the patient and the film.

It is a further object of the present invention to provide a system, as above, usable with x-ray equipment in which the components thereof are adjustably movable along a wall and yet readily and easily locked in place.

It is yet another object of the present invention to provide a system, as above, usable with x-ray equipment in which the majority of components thereof including the cylindrical x-ray tube itself may be removed from their position on a wall and stored when not in use so as not to waste valuable floor space.

It is an additional object of the present invention to provide a system, as above, which is inexpensive and easy to operate.

These and other objects of the present invention, as well as the advantages over existing prior art forms, which will become apparent from the description to follow, are accomplished by the invention hereinafter described and claimed.

In general, a system, made in accordance with the present invention, for mounting a cylindrical item to another member includes a plate which is attachable to the member. A slot in the plate extends in the longitudinal direction of the cylindrical item to be mounted. A clamp arm is carried by and spaced from the plate. With the cylindrical item positioned in the space between the plate and the clamp arm and longitudinally adjacent to the slot, the clamp arm may be rotated to hold the cylindrical item between the slot and the clamp arm.

The system is particularly suited for use with x-ray equipment wherein the cylindrical item is an x-ray tube. Such equipment includes a pair of tracks mounted on a wall in a spaced, parallel relationship. Each track carries a traveller assembly movable thereon. One traveller assembly carriers the mounting system for the x-ray tube and the other carries an x-ray received. Means are provided to align the traveller assemblies and, once aligned, means are provided to hold them in place on the tracks.

A preferred exemplary mounting system incorporating the concepts of the present invention is shown by way of example in the accompanying drawings without attempting to show all the various forms and modifications in which the invention might be embodied, the invention being measured by the appended claims and not by the details of the specification.

BRIEF DESCRIPTION OF THE DRAWINGS

FIG. 8 is a front elevational view similar to FIG. 6 but showing a cylindrical tube mounted in place.

FIG. 9 is an elevational view of depicting the manner in which the system of the present invention may be employed to mount cylindrical items, such as a pipe, to any generally flat surface, such as a wall.

PREFERRED EMBODIMENTS FOR CARRYING OUT THE INVENTION

Figure 1:
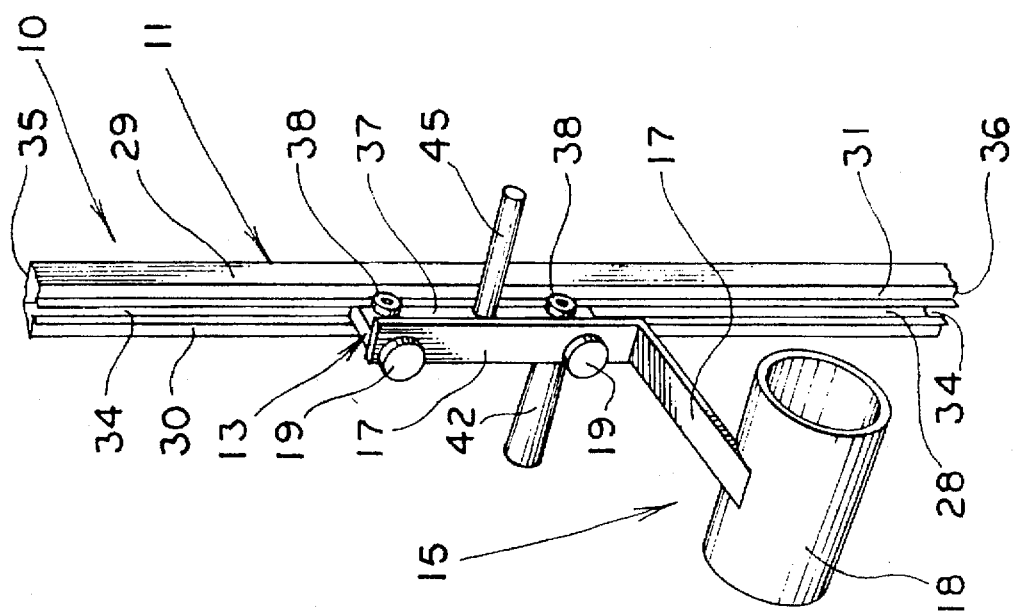
FIG. 1 is a fragmented perspective view of x-ray equipment of the type which may be provided with the system made in accordance with the present invention and which x-ray equipment includes tracks mounted on a wall and travellers positioned in the tracks.
Figure 1:
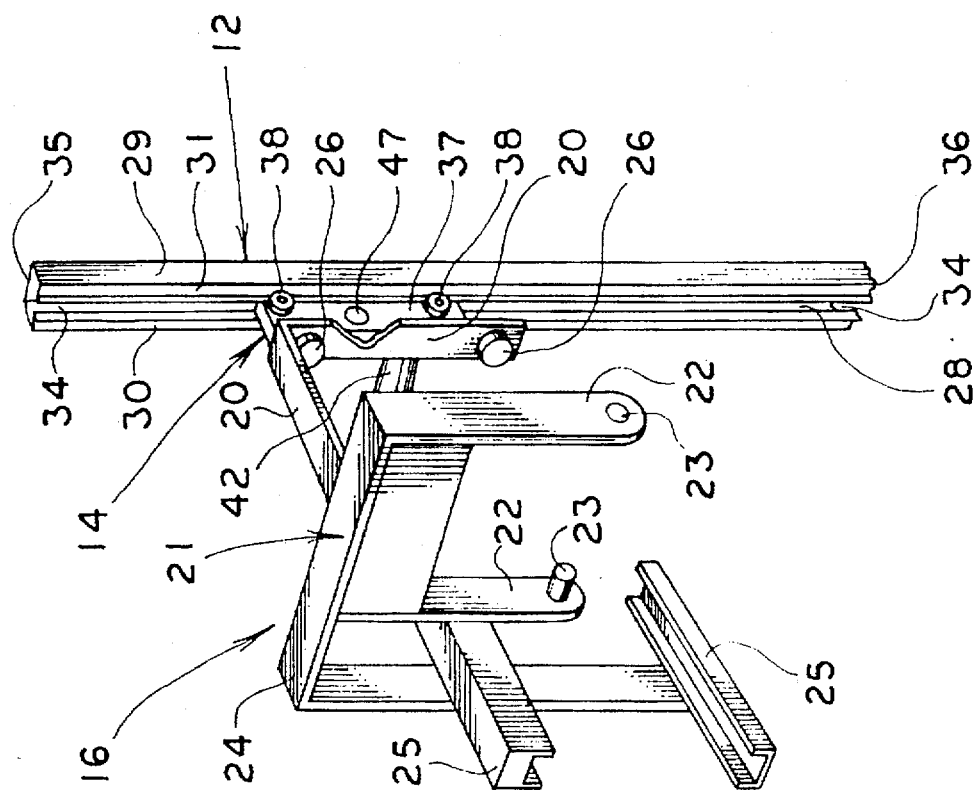

One embodiment of an x-ray system is indicated generally by the numeral 10 in FIG. 1 and includes a pair of tracks generally indicated by the numerals 11 and 12 and mounted in a vertical and parallel relationship on a wall. As will hereinafter become evident, tracks 11 and 12 are of length, and are mounted at a height, so as to extend through the normal range of human heights.

System 10 also includes a traveller assembly generally indicated by the numeral 13 and removably carried by track 11, and a traveller assembly generally indicated by the numeral 14 and removably carried by track 12. With one exception, to be hereinafter described, traveller assemblies 13 and 14 are identical in construction, but serve different functions. Traveller assembly 13 is adapted to carry x-ray source equipment, schematically shown and generally indicated by the numeral 15 in FIG. 1, and traveller assembly 14 is adapted to carry x-ray receiving and patient locating equipment, schematically shown and generally indicated by the numeral 16 in FIG. 1.

X-ray source equipment 15 includes an L-shaped bracket 17 which in this embodiment permanently carries a conventional x-ray tube 18 at a predetermined lateral distance away from track 11 and the wall. X-ray tube 18 is adapted to receive the conventional x-ray source (not shown). Bracket 17 may be attached to traveller assembly 13, as by thumb bolts 19.

X-ray receiving and patient locating equipment 16 includes an L-shaped bracket 20 which carries, in the instance of cephalometric x-rays, a U-shaped head positioning device 21 having downwardly directed branches 22 each carrying opposed ear pins 23. In practice, a patient's head is positioned between branches 22 with the patient's ears aligned with pins 23. The patient is then in the proper position for a cephalometric x-ray. It should be, or will become evident, however, that system 10 could be utilized to x-ray other portions of the anatomy, the vertical position of which varies depending on the size of the patient.

Equipment 16 also includes another L-shaped bracket 24 which can be carried by bracket 20. Bracket 24 carries opposed film holding plates 25 or like devices to hold the x-ray film adjacent to the patient's head. In practice, the film should be about five feet from the x-ray source so that tracks 11 and 12 are spaced from each other such that when bracket 20 is attached to traveller assembly 14, as by thumb bolts 26, film holding plates 25 are about five feet from x-ray tube 18.

Figure 2:
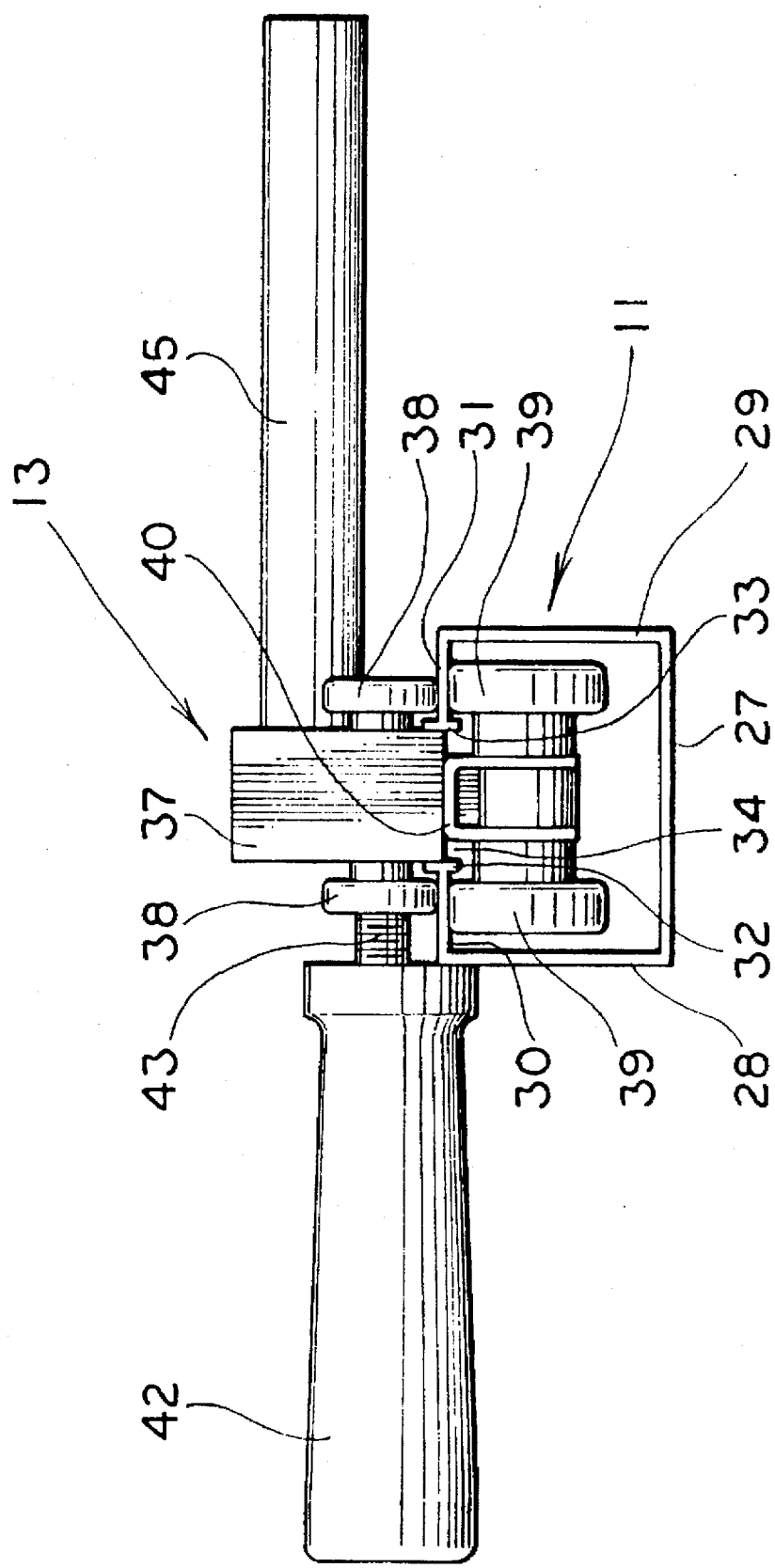
FIG. 2 is an end elevational view of a traveller in a track as shown in FIG. 1.

The configuration of identical tracks 11 and 12 is best shown in FIG. 2 with reference to an end view of track 11. Track 11 is a box-like structure having a rear wall 27 adapted to be attached to the wall of the room in any suitable fashion and side walls 28 and 29 extending laterally away from rear wall 27 and the wall of the room in which system 10 is installed. Track rails 30 and 31 are formed at the inner ends of walls 28 and 29, respectively, and extend toward each other and generally parallel to rear wall 27. Rails 30 and 31 terminate as opposed, spaced, guide flanges 32 and 33, respectively, which are generally parallel to side walls 28 and 29. Tracks 11 and 12 thus have a partially open front face, as at 34, between flanges 32 and 33. In addition, tracks 11 and 12 are each open at their top 35 and bottom 36 so that travellers 13 and 14 may be readily removed therefrom as will be hereinafter described.

Figure 3:
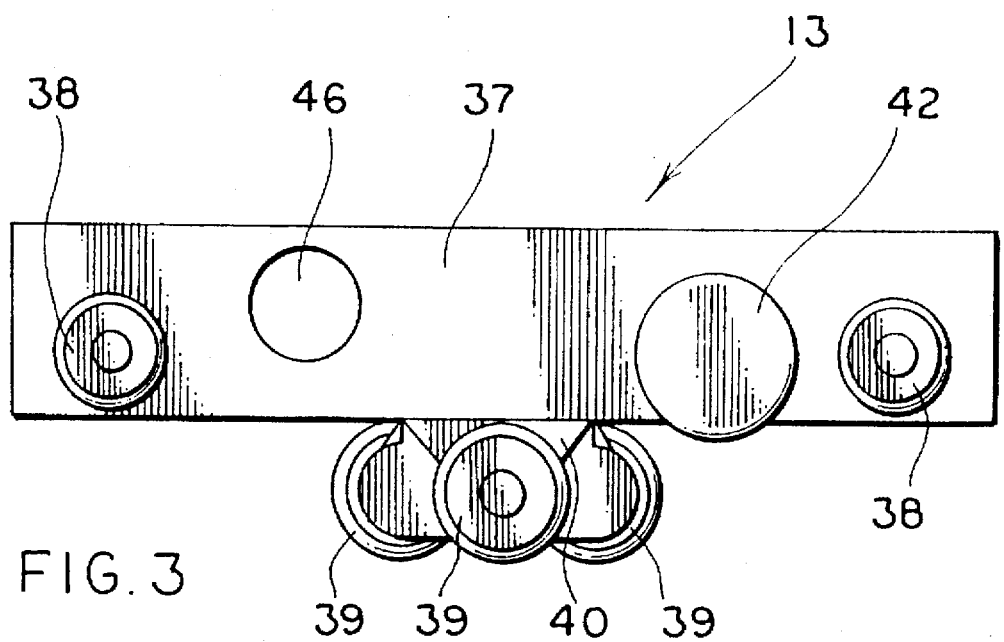
FIG. 3 is a side elevational view of a traveller of FIG. 1.
Figure 4:
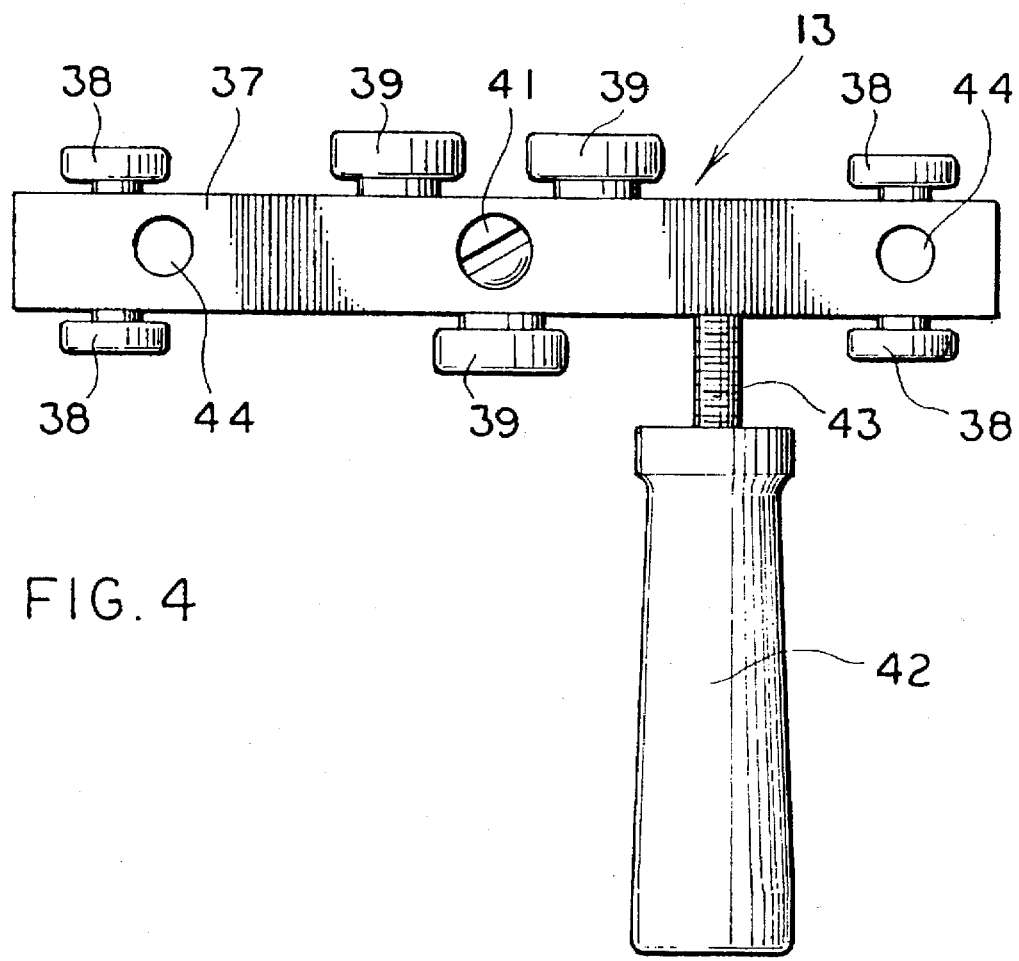
FIG. 4 is a front elevational view of the traveller of FIG. 3.

With particular reference to FIGS. 2-4, traveller assembly 13 is shown therein, and traveller assemblies 13 and 14 will now be described, keeping in mind that, as previously indicated, traveller assemblies 13 and 14, with the one exception discussed, are identical. Traveller assemblies 13 and 14 thus each include a main body portion 37 generally in the shape of a rectangular block. A pair of rollers 38 is carried hear each end of body portion 37 and, as shown in FIG. 2, rollers 38 are adapted to ride on the outside of rails 30 and 31. A grouping of three rollers 39 is positioned to ride on the inside of rails 30 and 31, although two opposed or four opposed rollers would operate just as well. Rollers 39 are carried by a bogie frame 40 which is attached, as by fastener 41 (FIG. 4), to body portion 37.

Rollers 38 and 39 are preferably made of a nylon material and are laterally spaced from each other a distance slightly less than the thickness of rails 30 and 31 as shown in FIG. 2. Travellers 13 and 14 are positioned on tracks 11 and 12 by threading rollers 39 through either open end 35 or 36 thereof with rails 30 and 31 between rollers 38 and 39 as shown in FIG. 2. As such, there is a fairly tight friction fit as rails 30 and 31 are engaged by rollers 38 and 39. Moreover, when so positioned, body portion 37 is relatively tightly received between guide flanges 32 and 33 which further stabilizes travellers 13 and 14 on tracks 11 and 12, respectively.

Nevertheless, with the assistance of a handle 42, the frictional fit between rollers 38 and 39 and rails 30 and 31 may be overcome, and travellers 13 and 14 may be manually positioned at any point along tracks 11 and 12, respectively. Handle 42 has a threaded shaft 43 which is received by body portion 37 of each traveller 13 and 14. When the desired vertical position of travellers 13 or 14 is reached, its handle 42 may be tightened so that it frictionally engages side wall 28 of tracks 11 and 12 as shown in FIG. 2.

Body portion 37 of travellers 13 and 14 also carries the x-ray receiving and patient locating equipment 16, respectively. To that end, body portion 37 is provided with threaded openings 44 (FIG. 4) to receive thumb bolts 19 and 26.

Travellers 13 and 14 each carry a different component of an alignment system which represents the only structural difference between travellers 13 and 14. Thus, traveller 13 is designed to carry an alignment source, which can be in the form of an optical or laser beam transmitter 45 carried by body portion 37 as shown in FIGS. 1 and 2. While such can be a permanent part of traveller 13, transmitter 45 can be in the form of the conventional portable laser pointer used, for example, by speakers during lectures. As such, it can be removably positioned in an aperture 46 (FIG. 3), extending through body portion 37, as desired. Traveller 14, however, is not provided with a transmitter 45 but rather has a receiver in the form of a target 47 (FIG. 1) to receive the beam of transmitter 45 to align travellers 13 and 14. Target 47 is at the same position of its body portion 37 as is the transmitter 45 of its body portion 37. Of course, other optical alignment systems could be substituted for laser beam transmitter 45 without departing from the spirit of the present invention. For example, simple ruler-like calibrations could be imprinted on tracks 11 and 12 for the positioning of travellers 13 and 14. Of course, such would require that tracks 11 and 12 be precisely positioned at the same height on the wall whereas, in the optical alignment system just described, such would not be mandatory.

In the operation and utilization of system 10, traveller 14, having equipment 16 attached thereto, is positioned onto track 12 and moved by grasping handle 42 until it is at the proper height: that is, with the patient standing adjacent to track 12 and the patient's ears aligned with pins 23. Then handle 42 is tightened against track side wall 28 to hold traveller 14 at the desired height and assure that it does not fall, under the weight of equipment 16, out of track 14. Then traveller 13, having equipment 15 attached thereto, is positioned in track 11 and by means of handle 42, and with beam transmitter 45 activated, it is moved along track 11 until the beam is squarely aligned with target 47 at which time handle 42 can be tightened against track side wall 28 to hold it in place. At this time, x-ray tube 18 is properly aligned with the patient and the x-ray may be taken.

When the system 10 is no longer needed, handles 42 may be loosened and travellers 13 and 14, and the equipment 15 and 16 that they are carrying, can be removed through either top openings 35 or bottom openings 36 of tracks 11 and 12, and the system can be stored in a convenient place. As such, it is not taking up space in the room adjacent to tracks 11 and 12 which can permanently remain on the wall. Or, if desired, the travellers 13 and 14 may be left on tracks 11 and 12 and the x-ray equipment merely removed therefrom, for storage, by loosening thumb bolts 19 and 26.

Figure 5:
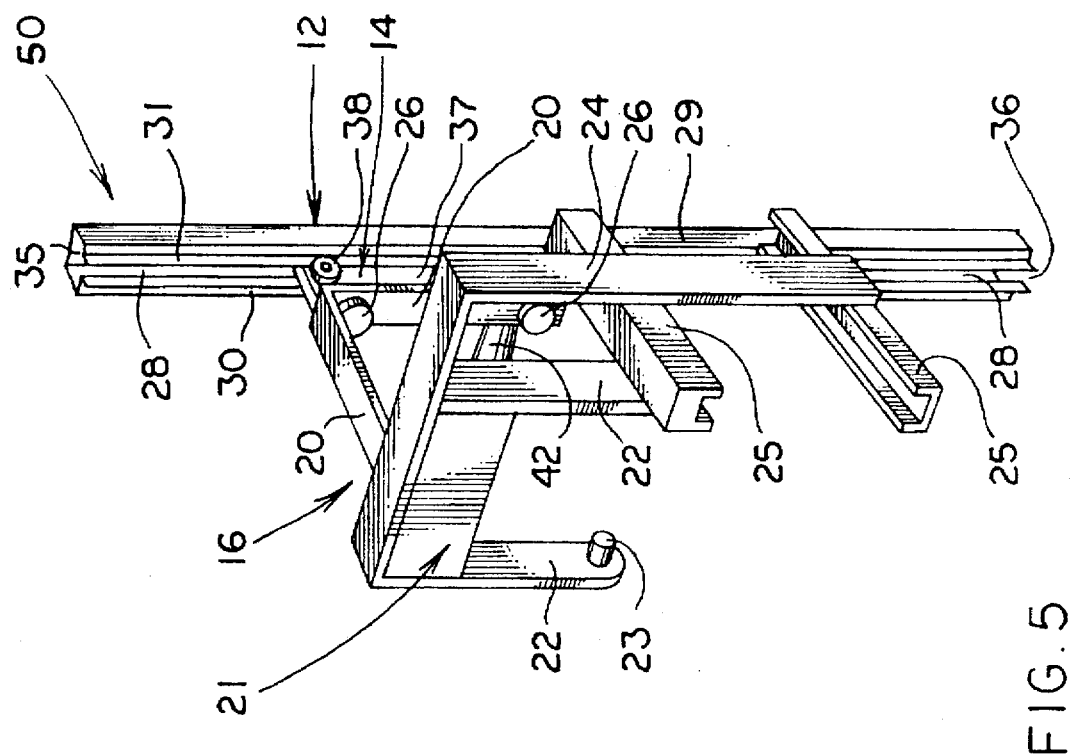
FIG. 5 is a fragmented perspective view of x-ray equipment similar to that of FIG. 1, but showing it as including a tube mounting system made in accordance with the concept of the present invention.
Figure 5:
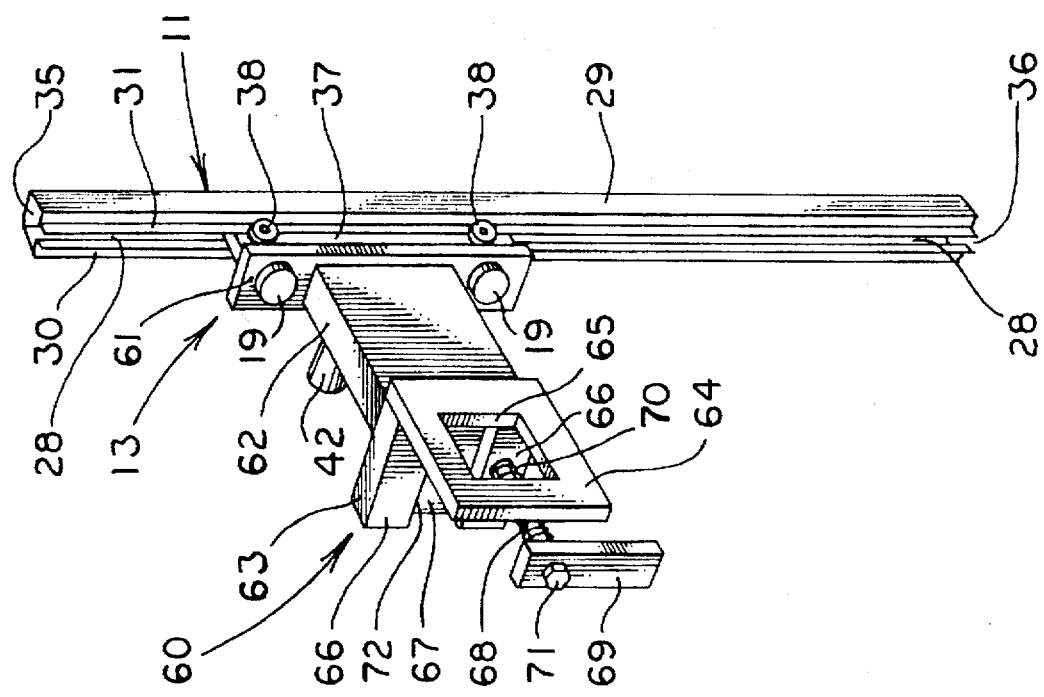

Another embodiment of an x-ray system is shown in FIG. 5 and indicated generally by the numeral 50. In almost all respects, x-ray system 50 is identical to x-ray system 10 and therefore like elements have been given the same reference numerals. Thus, x-ray system 50 includes tracks 11 and 12, travellers 13 and 14, and patient locating equipment 16 which all operate and are constructed as previously described with respect to x-ray system 10. However, in this embodiment the x-ray source equipment 15 is replaced by a mounting system made in accordance with the present invention and generally indicated by the numeral 60.

Mounting system 60, when used with x-ray system 50, includes a plate 61 which may be attached to traveller assembly 13 as by the thumb bolts 19 previously described. An arm 62 extends laterally outwardly from plate 61 and carries a mounting plate 63 which extends transversely of arm 62. A wave-shaping plate 64 extends laterally outwardly from one edge of mounting plate 63 and has a square aperture 65 therein to properly collimate the x-ray beam for a cephalometric x-ray. The face 66 of mounting plate 63 is provided with a slot 67, preferably rectangular in profile, extending from side to side therein. Face 66 of plate 63 also receives a threaded member, such as the body portion of bolt 68 therethrough. A clamp arm 69 is slidably received on bolt 68 and a spring 70 positioned around bolt 68 maintains arm 69 positioned laterally outward against the head 71 of bolt 68 to maintain arm 69 spaced from mounting plate 63. With the exception of bolt 68 and spring 70, all of the components of system 60, and in particular arm 69, may be made of a high density polypropylene material or any equivalent material having some degree of resilience, for reasons to be hereinafter discussed.

Figure 7:
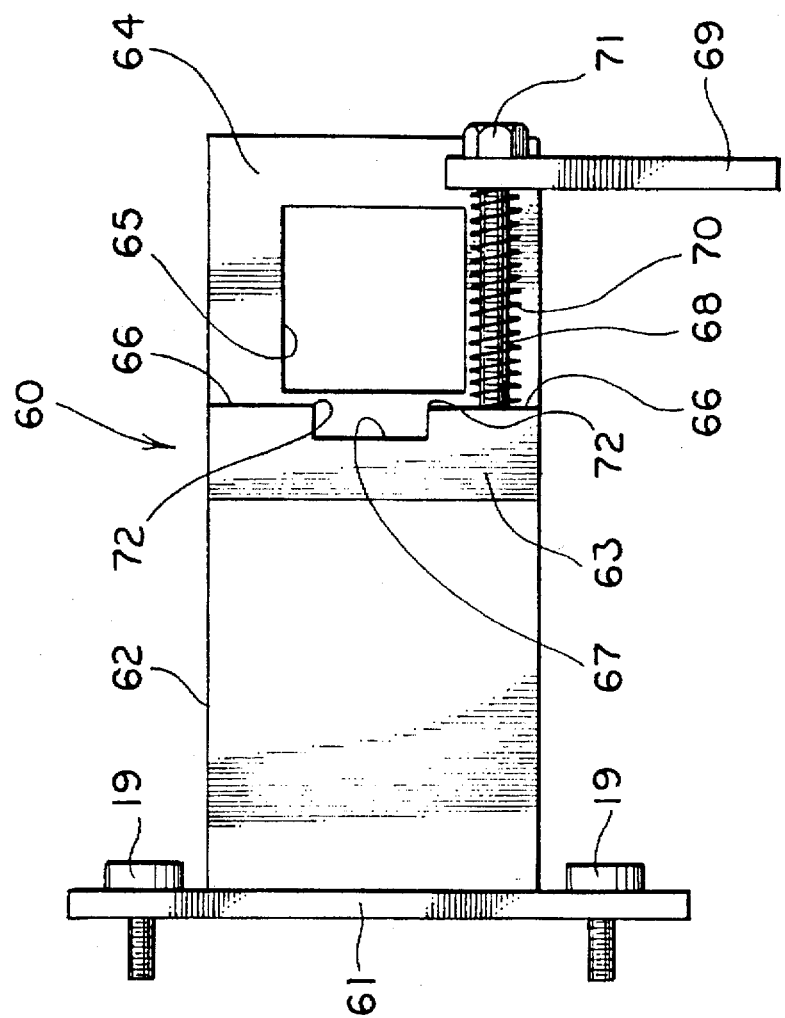
FIG. 7 is a side elevational view of the tube mounting system shown in FIGS. 5 and 6.
Figure 6:
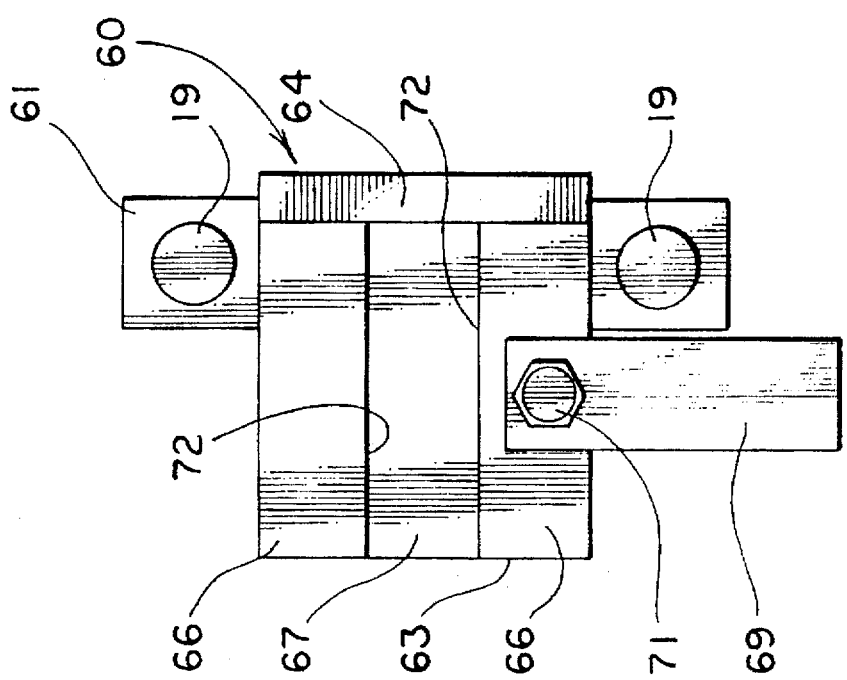
FIG. 6 is a front elevational view of the tube mounting system shown in FIG. 5.

Mounting system 60 is adapted to carry and firmly, yet releasably, hold the conventional cylindrical x-ray tube or cone 18, as shown in FIG. 8, in a manner now to be described. As shown in FIGS. 5–7, when system 60 is empty, that is, not carrying tube 18, arm 69 hangs downwardly under the influence of gravity. The distance between arm 69 and mounting plate 63 may be adjusted to accommodate x-ray tubes of differing diameters by turning bolt 68 to thereby thread it into or out of mounting plate 63. Once that distance is set, usually at a point slightly less than the diameter of tube 18, tube 18 may then be positioned with a lateral edge against wave-shaping plate 64 and with its circumferential longitudinal body extending along slot 67 of mounting plate 63. Arm 69 may then be rotated 180 degrees on bolt 68, to the FIG. 8 position, and tube 18 is thereby clamped between arm 69 and mounting plate 63. Specifically, because of the resiliency of arm 69, it will flex somewhat as it is being rotated to laterally confine tube 18, and because the circumferential body of tube 18 is engaged by the spaced edges 72 of slot 67, tube 18 is also vertically restrained.

Based on the foregoing, it should be evident that mounting system 60 enables the user to quickly mount an x-ray tube on, or dismount it from, x-ray equipment, such as x-ray system 50 or like devices. As such, the tube is thus rendered portable and is not dedicated to one machine, but rather can be used in other equipment as well. Moreover, as described above, system 60 is readily adjustable to hold x-ray tubes of varying diameters merely by utilizing bolt 68 to adjust the position of arm 69 relative to mounting plate 63, with arm 69 being maintained at the desired position by virtue of the bias of spring 70. Also, because the tube is maintained in a proper vertical position by spaced edges 72 of slot 67, tubes of varying diameters are likewise accommodated.

In fact, the concept of system 60, with some modification, can be utilized to, at least temporarily, affix any tubular or cylindrical item to any noncylindrical surface. For example, as shown in FIG. 9, one or more systems 60 could be utilized to at least temporarily mount a pipe 73 on a wall. In this application, plate 61, arm 62 and wave-shaping plate 64 are not necessary items. Rather, mounting plate 63 with its slot 67 may merely be attached to the wall, bolt 68 adjusted to space arm 69 the desired distance from mounting plate 63 depending on the diameter of pipe 73, and arm 69 rotated to clamp pipe 73. Dependent on the length of pipe 73, it may be desired, as shown in FIG. 9, to space a plurality of mounting systems 60, with the slots 67 of plates 63 aligned, along the wall for complete support.

It should thus be apparent that a tube mounting system as described herein can be useful to mount a cylindrical item to a noncylindrical surface and is particularly useful to mount an x-ray tube to x-ray equipment, thus substantially improving the art and otherwise accomplishing the objects of the present invention.

I claim:

1. A system for mounting a cylindrical item to another member comprising a plate attachable to the member, a slot in said plate extending in a direction, a resilient clamp arm, means to space said clamp arm at a predetermined distance from said plate and to rotatably carry said clamp arm, the cylindrical item being positionable in the space between said clamp arm and said plate longitudinally in the direction adjacent to said slot, such that upon rotation of said clamp arm, the predetermined distances does not change yet the cylindrical item is held between said clamp arm and said slot.

2. A system according to claim 1 wherein said means is movable so that the predetermined distance is adjustable.

3. A system according to claim 1 wherein said means is a bolt threaded into said plate.

4. A system according to claim 3 wherein said bolt has a threaded body position and a head spaced from said plate by said body portion, and further comprising spring means around said body portion to bias said clamp arm against said head.

5. A system according to claim 1 wherein the rotation of said clamp arm positions said clamp arm in a direction generally laterally of the direction.

6. A system according to claim 1 wherein said slot is generally rectangular in profile having edges engageable with the cylindrical item.

7. A system according to claim 1 wherein the member is a wall and further comprising at least a second plate attachable to the wall and spaced from said plate, a slot in said second plate extending in the direction and aligned with said slot in said plate, a clamp arm for said second plate, and means to space said clamp arm for said second plate from said second plate and to rotatably carry said clamp arm for said second plate, the cylindrical item being positionable longitudinally in the direction adjacent to said slots and in the space between said clamp arm and said plate as well as in the space between said clamp arm for said second plate and said second plate, such that upon rotation of said clamp arms, the cylindrical item is held between said clamp arms and said slots and spans the distance between said plate and said second plate.

8. A system for mounting an x-ray tube to an arm of x-ray equipment comprising a first plate attachable to the x-ray equipment a slot in said first plate extending in a direction, a clam arm, means to space said clamp arm from said first plate and to rotatably carry said clamp arm, the x-ray tube being positionable in the space between said clamp arm and said first plate longitudinally in the direction adjacent to said slot such that upon rotation of said clam arm, the x-ray tube is held between said clamp arm and said slot, and a second plate extending laterally from said first plate and having an x-ray beam aperture therein, a longitudinal edge of the tube being positioned against said second plate when the tube is held between said clamp arm and said slot.

9. A system according to claim 8 wherein said aperture is generally square to collimate the x-ray beam.

10. A wall-mountable x-ray system comprising a first track mountable on a wall, a second track mountable on the wall spaced from and parallel to said first track, first traveller means movable on said first track, mounting means for at least temporarily attaching a cylindrical x-ray tube to said first traveller means, second traveller means movable on said second track and adapted to carry an x-ray receiver, means to align said first and second traveller means, and means to hold said first and second traveller means at their aligned position.

11. An x-ray system according to claim 10 wherein said means to align includes an optical source carried by said first traveller means and optical receiving means carried by said second traveller means.

12. An x-ray system according to claim 10 wherein said mounting means includes a plate carried by said first traveller, and a clamp arm carried by and spaced from said plate, said tube being positionable between said clamp arm and said plate.

13. An x-ray system according to claim 12 wherein said clamp arm is made of a resilient material.

14. An x-ray system according to claim 12 further comprising a second plate extending laterally from said plate and having an x-ray beam aperture therein, a longitudinal edge of said tube being positioned against said second plate when said tube is held between said clamp arm and said plate.

15. An x-ray system according to claim 12 further comprising a slot in said plate extending in the longitudinal direction of said tube.

16. An x-ray system according to claim 15 further comprising means to space said clamp arm from said plate, said clamp arm being rotatably carried on said means to space so that upon rotation of said clamp arm said tube is held between said slot and said clamp arm.

17. An x-ray system according to claim 16 wherein said means to space includes a bolt threaded into said plate, rotation of said bolt thereby adjusting the space between said plate and said clamp arm.

18. A system according to claim 17 wherein said bolt has a threaded body position and a head spaced from said plate by said body portion, and further comprising spring means around said body portion to bias said clamp arm against said head.

19. An x-ray system according to claim 10 wherein said mounting means includes a first plate carried by said first traveller means, an arm extending outwardly from said first plate, a second plate carried by said arm and a clamp arm carried by and spaced from said second plate, said tube being positionable between said clamp arm and said second plate.

20. An x-ray system according to claim 10 wherein said means to hold also facilitates movement of said traveller means on said tracks.

21. An x-ray system according to claim 20 wherein said means to hold includes a handle carried by each said traveller means, and means to vary the position of each said handle relative to each said traveller.

* * * * *